US009090521B2

(12) United States Patent
Al-Haji (10) Patent No.: US 9,090,521 B2
(45) Date of Patent: Jul. 28, 2015

(54) RECOVERY METHOD AND SYSTEM FOR DELIVERING EXTRACTED BTX FROM GAS STREAMS

(71) Applicant: Saudi Arabian Oil Company, Dhahran (SA)

(72) Inventor: Mohammad N. Al-Haji, Dammam (SA)

(73) Assignee: SAUDI ARABIAN OIL COMPANY (SA)

( * ) Notice: Subject to any disclaimer, the term of this patent is extended or adjusted under 35 U.S.C. 154(b) by 0 days.

(21) Appl. No.: 13/828,700

(22) Filed: Mar. 14, 2013

(65) Prior Publication Data

US 2013/0245351 A1   Sep. 19, 2013

Related U.S. Application Data

(60) Provisional application No. 61/611,855, filed on Mar. 16, 2012.

(51) Int. Cl.
*C07C 7/11* (2006.01)
*C07C 7/04* (2006.01)
*B01D 53/14* (2006.01)

(52) U.S. Cl.
CPC .............. *C07C 7/11* (2013.01); *B01D 53/1425* (2013.01); *B01D 53/1487* (2013.01); *C07C 7/04* (2013.01); *B01D 2252/2056* (2013.01); *B01D 2257/7027* (2013.01)

(58) Field of Classification Search
None
See application file for complete search history.

(56) References Cited

U.S. PATENT DOCUMENTS

| 2,974,750 A | 3/1961 | Retallick |
| 4,528,001 A | 7/1985 | Yokogawa et al. |
| 5,039,319 A | 8/1991 | Glass et al. |

FOREIGN PATENT DOCUMENTS

WO   2007003618 A1   1/2007

OTHER PUBLICATIONS

PCT Notification of Transmittal of the International Search Report and the Written Opinion of the International Searching Authority, or the Declaration; dated May 27, 2013; International Application No. PCT/US2013/030714; International File Date: Mar. 13, 2013.

*Primary Examiner* — Tam M Nguyen
(74) *Attorney, Agent, or Firm* — Bracewell & Giuliani LLP; Constance Gall Rhebergen; Brad Y. Chin (57) ABSTRACT

A recovery method and a system for delivering extracted benzene, toluene, and xylene from a hydrocarbon gas stream is provided. The method includes introducing a feed stream of a BTX-rich hydrocarbon gas into an absorber. The method further includes combining, in the absorber, the hydrocarbon gas with an aprotic solvent, such that the hydrocarbon gas and the aprotic solvent are thoroughly intermixed so that the BTX is absorbed into the aprotic solvent, resulting in the production of a BTX-rich solvent and a substantially BTX-free gas. The method further includes vaporizing, using a vaporizer, the BTX-rich solvent to produce a vaporized BTX-rich solvent, and separating, using a distiller, the BTX from the vaporized BTX-rich solvent for delivering the extracted BTX from the hydrocarbon gas. The separation of the BTX from the vaporized BTX-rich solvent also produces a BTX-lean solvent that is recycled back into the absorber as the aprotic solvent.

9 Claims, 7 Drawing Sheets

PRIOR ART

PRIOR ART

FIG. 1c

PRIOR ART

RECOVERY METHOD AND SYSTEM FOR DELIVERING EXTRACTED BTX FROM GAS STREAMS

RELATED APPLICATION

This application is related to, and claims priority to, U.S. Provisional Patent Application Ser. No. 61/611,855, filed on Mar. 16, 2012, the disclosure of which is incorporated by reference in its entirety.

BACKGROUND

1. Field of the Invention

Embodiments of the invention generally relate to a recovery method and system for delivering extracted benzene, toluene and xylene (BTX) from hydrocarbon gas streams. More particularly, embodiments of the invention relate to a recovery method and system for delivering an extracted BTX component from a BTX-rich hydrocarbon gas stream that includes contacting, for example, in an amine-free environment, a BTX-rich hydrocarbon gas feed stream with an aprotic solvent to produce a BTX-free gas and a BTX component.

2. Description of the Related Art

Gas streams in processing facilities, such as refineries, olefins plants, and other industrial settings sometimes contain aromatics, such as BTX. BTX is typically removed from the gas stream to avoid impacting the reliability of certain processing equipment in the path of the steam that may be sensitive to BTX. Moreover, when the gas stream is a sales gas used as fuel, such as by a utility or other energy generator, BTX components can negatively affect equipment handling the sales gas.

Figure 1A:
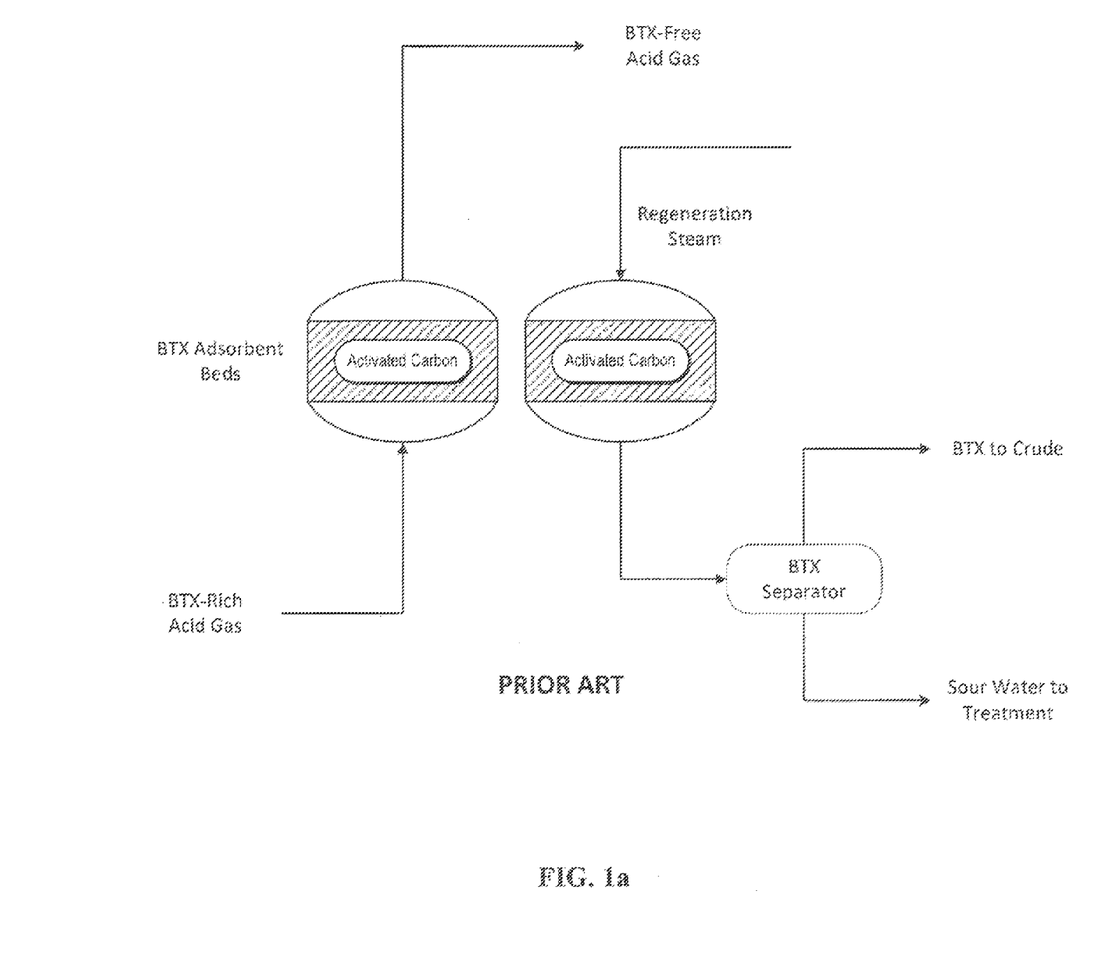
FIG. 1a is a schematic diagram of a conventional process for removing BTX from a gas stream using feed media adsorption.
Figure 1B:
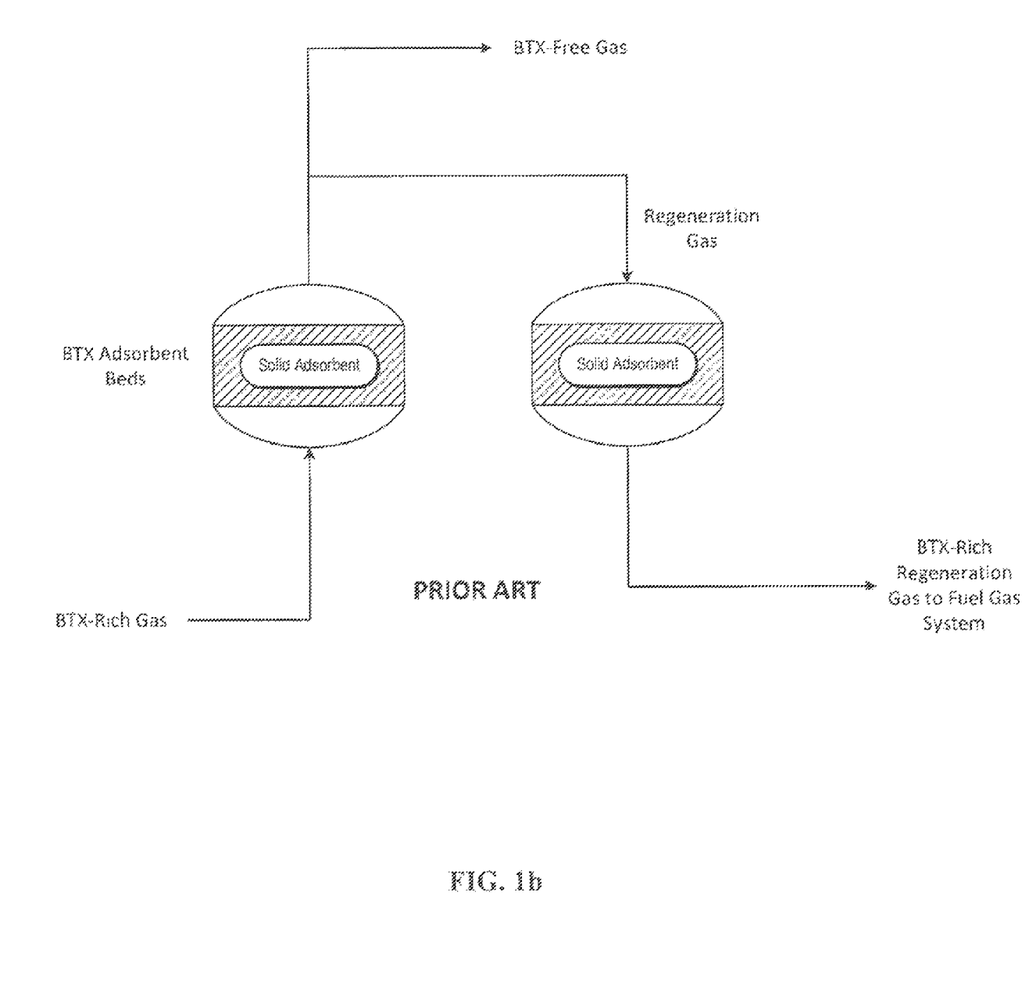
FIG. 1b is a schematic diagram of another conventional process for removing BTX from a gas stream using fixed media adsorption.

Fixed media adsorption is one technique used in conventional systems, as shown in FIGS. 1a and 1b, to remove BTX from a gas stream, where the media can be, for example, an activated carbon bed, as shown in FIG. 1a, a molecular sieve, as shown in FIG. 1b, or other adsorbent. Conventional adsorption methods using fixed media are typically expensive and require that the media be regenerated at some point to remove the adsorbed BTX. Regenerating adsorption media typically requires taking the media out of service for a period of time, or alternatively, a parallel circuit is required to continue operating, while the primary circuit is undergoing regeneration. Additionally, when regenerating the adsorption media, the removed BTX is contained in the regeneration fluid. Accordingly, a separate process is generally required to remove the BTX from the regeneration fluid. Regeneration fluids are often one of a regeneration gas or a regeneration steam. When regeneration steam is used, a separator is included that allows sour water to fall out of the flow, which can be sent to a treatment plant, while the removed BTX is part of a stream that is directed to a crude unit. In these conventional systems, while the BTX is removed from the gas stream, the extracted BTX component is consumed and therefore cannot be recovered for use as a petrochemical feedstock or for other commercial uses.

Figure 1C:
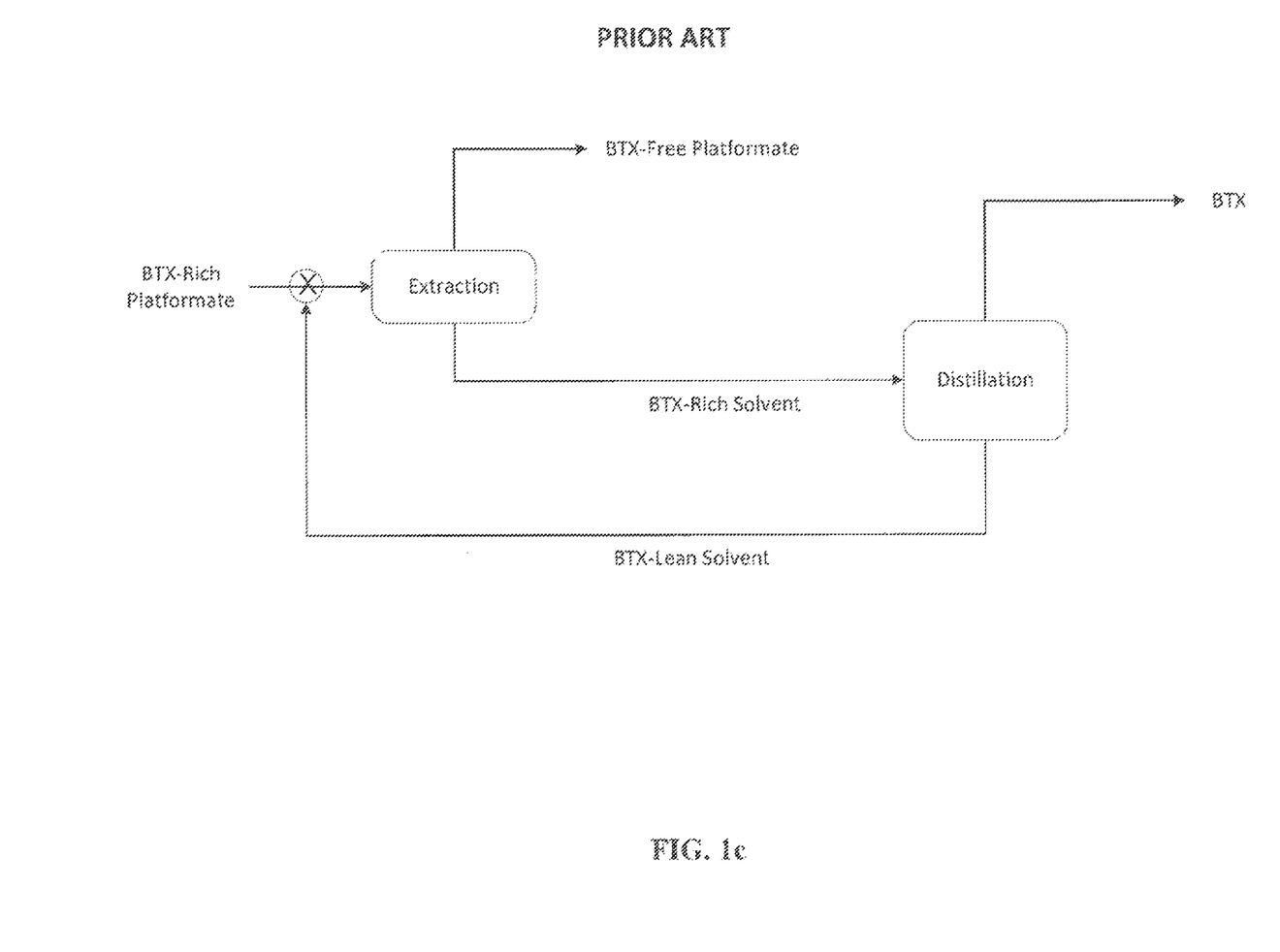
FIG. 1c is a schematic diagram of a conventional process for extracting BTX from refinery liquid streams using liquid-liquid extraction and distillation.
Figure 1D:
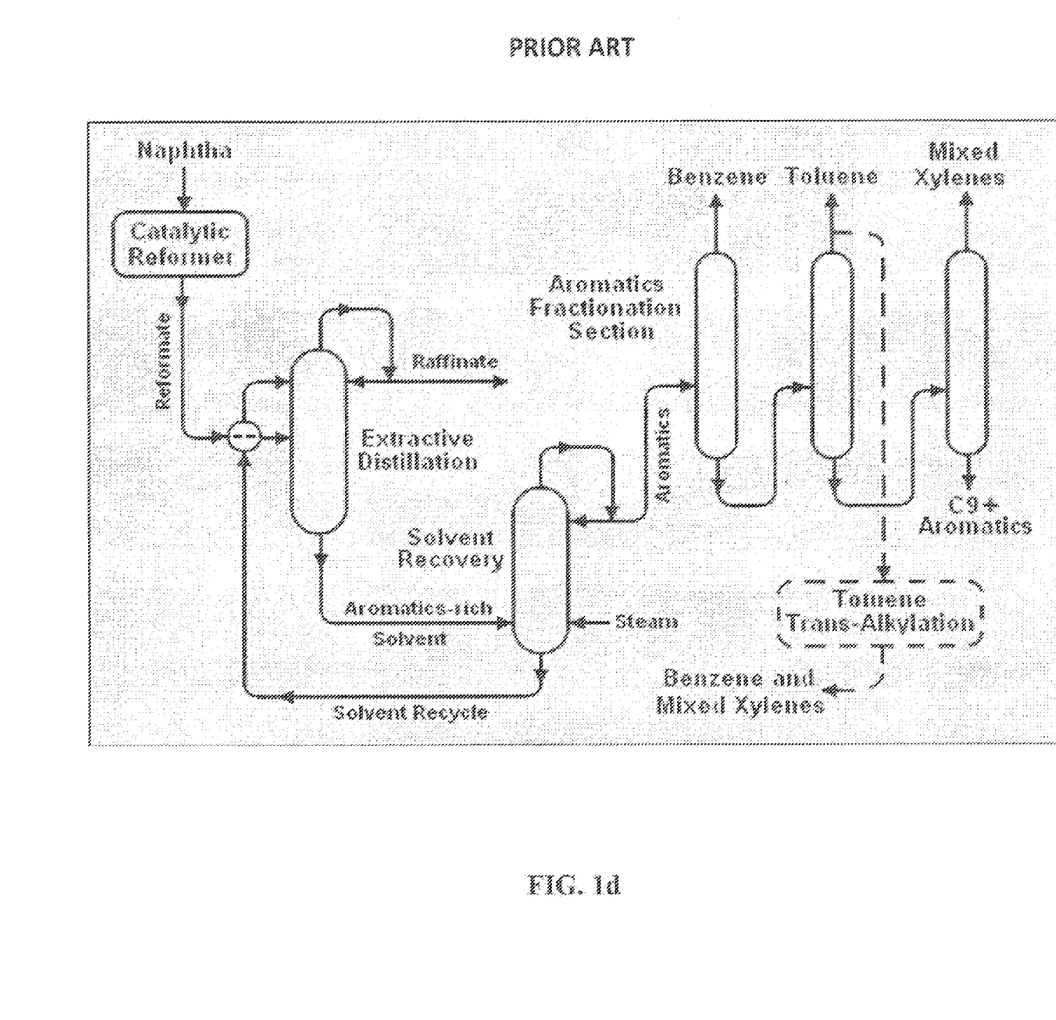
FIG. 1d is a schematic diagram of another conventional process for extracting BTX from refinery liquid streams using liquid-liquid extraction and distillation.

Extractive distillation is another technique used in conventional systems, as shown in FIGS. 1c and 1d, to remove BTX, but is limited to use for extracting BTX from a liquid stream, such as a refinery or petrochemical aromatic-containing liquid stream, for example, naphtha, which contains non-aromatic hydrocarbons. In these conventional systems, as shown in FIGS. 1c and 1d, the BTX-rich liquid steam may be fed to a catalytic reformer to produce a reformate product containing $C_6$ to $C_8$ aromatics (BTX), paraffins, and heavier aromatics containing 9 to 12 carbon atoms. A solvent, for example, in aprotic (i.e., non-$H^+$ donating ion) organosulfur compound, may be used to extract BTX from the BTX-rich liquid stream (e.g. platformate) using, for example, a contacting column, such as a liquid-liquid extraction unit, to generate a BTX-rich solvent from the bottom of the contacting column. The BTX-rich solvent is subsequently distilled using a distillation tower, where BTX is separated from the BTX-rich solvent.

SUMMARY

Embodiments of the invention are directed to methods and systems for delivering an extracted BTX component from a BTX-rich hydrocarbon gas stream that includes contacting, in an amine-free environment, a BTX-rich hydrocarbon gas feed stream with an aprotic solvent to produce a BTX-free gas and a BTX component. Because it is not consumed, the BTX component can be recovered, for example, for use as a petrochemical feedstock or for other commercial uses.

In accordance with certain embodiments of the invention, the BTX-rich hydrocarbon gas feed stream is contacted with a circulating aprotic solvent, for example, an organosulfur compound, preferably sulfolane, in a gas-liquid contactor vessel, for example, a gas-liquid absorption contacting column, where substantially all of the BTX from the BTX-rich hydrocarbon gas feed stream is absorbed into the aprotic solvent to produce a BTX-rich solvent.

In accordance with an embodiment of the invention, the aprotic solvent is introduced into the gas-liquid contactor vessel at a location above where the BTX-rich hydrocarbon gas feed stream is injected, so that the gas feed stream and the aprotic solvent contact one another as the gas feed stream flows upward in the gas-liquid contactor vessel and the aprotic solvent flows downward. The BTX-free gas exits an upper end of the gas-liquid contactor vessel, where it is substantially free of the BTX.

The BTX-rich solvent is fed to a flash drum to remove co-absorbed light hydrocarbons, where the residual BTX-rich solvent is subsequently directed to a distillation tower to separate the BTX component from the BTX-rich solvent. The resulting BTX-lean solvent is then redirected back into the gas-liquid absorption contacting column, where it contacts the BTX-rich hydrocarbon gas feed stream flowing into the contactor vessel.

In accordance with other embodiments of the invention, the methods and systems are operable to treat the BTX-rich gas feed stream with the aprotic solvent in an amount sufficient to achieve approximately 99.6% and appropriately 99.1% removal of BTX and benzene, respectively.

In accordance with an embodiment of the invention, there is provided a method for delivering extracted BTX from a hydrocarbon gas stream. The method includes introducing a feed stream of a hydrocarbon gas including BTX into an absorber. The method further includes combining, in the absorber, the hydrocarbon gas with an aprotic solvent, such that the hydrocarbon gas and the aprotic solvent are thoroughly intermixed, so that the BTX is absorbed into the aprotic solvent, resulting in a BTX-rich solvent, and vaporizing, using a vaporizer, the BTX-rich solvent to produce a vaporized BTX-rich solvent. Further, the method includes separating, using a distiller, the BTX from the vaporized BTX-rich solvent for delivering the extracted BTX from the hydrocarbon gas. The separation of the BTX from the vaporized BTX-rich solvent also produces a BTX-lean solvent that is recycled back into the absorber as the aprotic solvent.

In accordance with another embodiment of the invention, there is provided a recovery system for delivering extracted BTX from a hydrocarbon gas stream. The recovery system includes an absorber including a gas inlet that receives a hydrocarbon gas. The hydrocarbon gas includes a high content of BTX. The absorber further includes a liquid inlet that receives a solvent. The solvent includes an aprotic solvent having a low BTX content. The absorber is operable to combine the hydrocarbon gas with the aprotic solvent, such that the hydrocarbon gas and the aprotic solvent are thoroughly intermixed, so that BTX is absorbed into the aprotic solvent to produce a BTX-rich solvent. The recovery system further includes a vaporizer that vaporizes the BTX-rich solvent to produce a vaporized BTX-rich solvent. The recovery system further includes a distiller that separates the BTX from the vaporized BTX-rich solvent to deliver the extracted BTX from the hydrocarbon gas. The recovery system is operable to recycle a BTX-lean solvent that is produced when the BTX is separated from the vaporized BTX-rich solvent back into the absorber as the aprotic solvent.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

DETAILED DESCRIPTION

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments.

Figure 2:
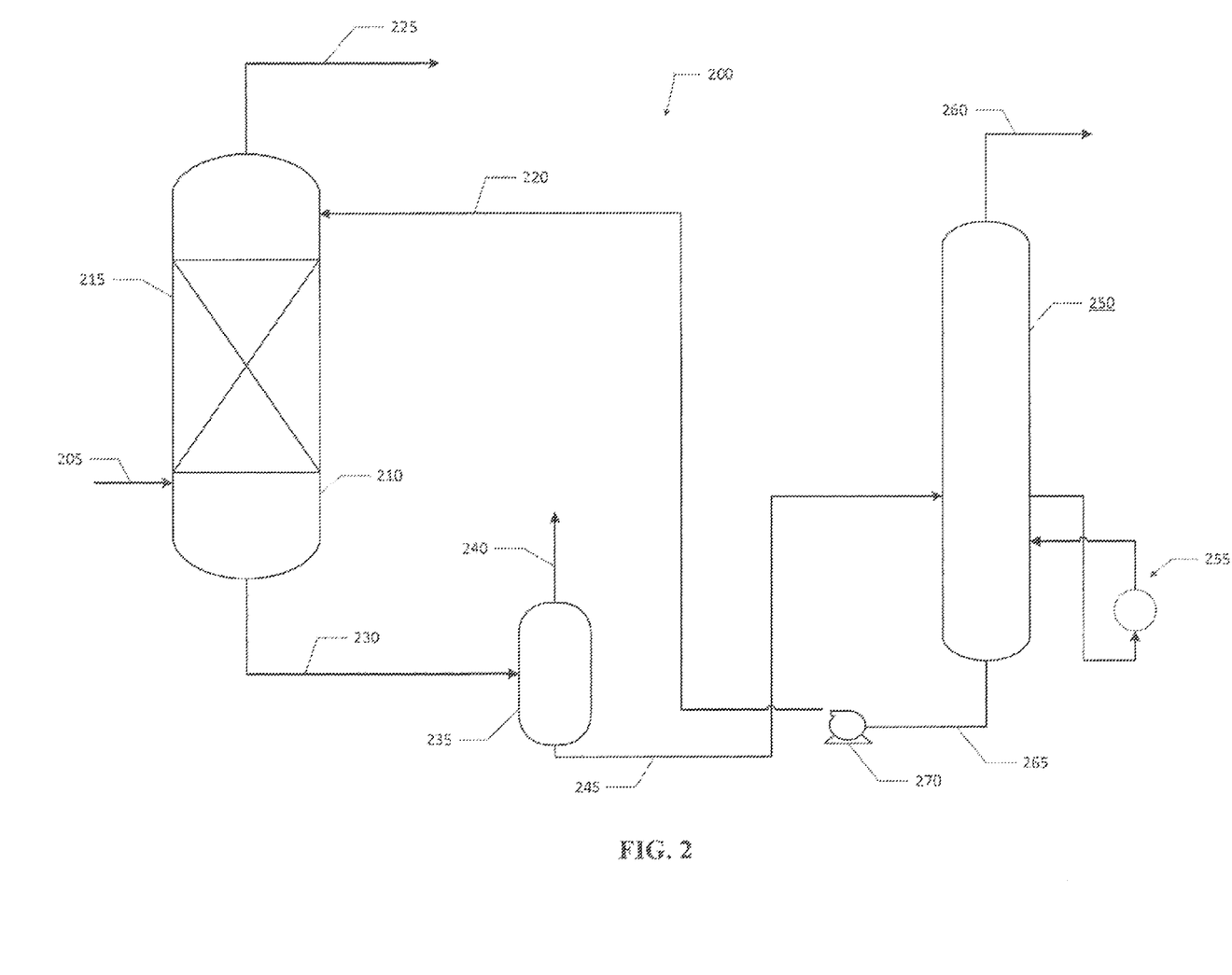
FIG. 2 is a schematic diagram of a recovery system for delivering extracted BTX from a hydrocarbon gas stream, in accordance with an embodiment of the invention.

FIG. 2 is a schematic diagram of a recovery system for delivering extracted BTX from a hydrocarbon gas stream, in accordance with an embodiment of the invention. The recovery system 200 is operable to deliver extracted BTX from a feed stream line 205 that contains a hydrocarbon gas having BTX content. The feed stream line 205 feeds into an absorption column 210 in which the BTX is extracted from the hydrocarbon gas in the feed stream line 205. The absorption column 210, for example, a gas-liquid absorption column, includes a plurality of trays 215 creating a tortuous path axially through the absorption column 210. In one embodiment, the absorption column 210 includes fifteen mass transfer trays 215, as a non-limiting example. As further illustrated in FIG. 2, a reflux line 220 includes a discharge end connected to the absorption column 210. The reflux line 220 will be discussed in more detail below.

As further shown in FIG. 2, the feed stream line 205 is coupled to the absorption column 210 at a location below the mass transfer trays 215, whereas the solvent line 220 is coupled to the absorption column 210 above the mass transfer trays 215. In other embodiments, the reflux line 220 is coupled to the absorption column 210 above where the feed stream line 205 is coupled to the absorption column 210. Accordingly, as the hydrocarbon gas exits from within the feed stream line 205 into the absorption column 210, the hydrocarbon gas flows upward within the absorption column 210 and contacts the fluid (e.g., BTX-lean solvent) that exits the reflux line 220 into the absorption column 210 and flows downward within the absorption column 210. In accordance with an embodiment of the invention, the solvent in the reflux line 220 includes an organosulfur solvent preferably including an aprotic solvent. For example, in one embodiment the solvent is made up of 2,3,4,5-tetrahydrothiophene-1,1-dioxide, which is also referred to as tetramethylene sulfone, or known by its trade name sulfolane.

As discussed above, the recovery system 200 is capable of extracting substantially all of the BTX, for example, at least 96% of the BTX, in the BTX-rich hydrocarbon gas using an aprotic solvent that is deposited into the absorption column 210 from the reflux line 220. Upon reaching a head space in an upper end of the absorption column 210, the BTX-rich hydrocarbon feed gas is substantially free of BTX (i.e., less than 4% of the BTX remaining in the BTX-rich hydrocarbon feed gas) ("BTX-free gas").

As further shown in FIG. 2, a treated gas line 225 extends from the upper end of the absorption column 210 to transport the BTX-free gas to another location within the processing facility, for example, for use as a petrochemical feedstock or for other commercial uses. BTX extracted from the BTX-rich hydrocarbon feed gas is absorbed into the solvent to produce a BTX-rich solvent that collects in a lower end of the absorption column 210. An absorption bottoms line 230 is coupled to a lower end of the absorption column 210 and directs the BTX-rich solvent through the absorption bottoms line 230 to a flash drum 235 that is operable to remove co-absorbed light hydrocarbons from the BTX-rich solvent. The system 200 further includes a flash drum line 240 on an upper end of the flash drum 235 that provides a conduit for escaping vapors to be directed to another part of the process facility (not shown). The system 200 further includes a flash drum bottoms line 245 coupled to a lower end of the flash drum 235 for directing the BTX-rich solvent in the flash drum 235 to a distillation tower 250 for further separating BTX from the BTX-rich solvent to produce a BTX component and a BTX-lean solvent. According to certain embodiments of the invention, the BTX-rich solvent directed from the lower end of the flash drum 235 is distilled in the distillation tower 250, whereby most of the BTX in the BTX-rich solvent separates from the solvent and migrates to an upper portion of the distillation tower 250. In accordance with at least one embodiment, the flash drum 235 is operated at about 100° F. and about 100 psig.

In accordance with another embodiment of the invention, the recovery system 200 includes a reboiler 255, for example, a thermosiphon reboiler, to inject heat into the distillation tower 250. As further shown in FIG. 2, a distillation overhead line 260 is coupled to an upper end of the distillation tower 250, through which the separated BTX in the distillation tower 250 is directed to another pan of the process facility (not shown), for example, for use as a petrochemical feedstock or for other commercial uses. As further shown in FIG. 2, the system 200 further includes a bottoms line 265 coupled to a lower end of the distillation tower 250 to direct the BTX-lean solvent from the distillation tower 250 to an optional pump 270 for pressurising the BTX-lean solvent before directing the BTX-lean solvent to the absorption column 210. For example, in accordance with an embodiment, the pump 270 discharges the pressurized BTX-lean solvent into the reflux line 220 at a pressure sufficient to overcome pressure losses in the reflux line 220, static head up to a nozzle (not shown) in the absorption column 210, and exit losses through the nozzle. In one embodiment, the absorption column 210 operates, for example, at a pressure of about 800 to about 900 psig, which is accounted for in the discharge pressure in the pump 270. In accordance with at least one embodiment, the absorption column 210 is operated at about 100° F.

As shown in FIG. 2, in accordance with certain embodiments of the invention, the bottoms line 265 and the pump 270 provide a way of recycling the BTX-lean solvent back to the absorption column 210 through the reflux line 220. By removing substantially all of the BTX from the BTX-rich solvent (i.e., to produce a BTX-lean solvent), when the BTX-lean solvent is reintroduced into the absorption column 210, the BTX-lean solvent can then be used to extract BTX from the hydrocarbon gas flowing through the feed steam line 205 and into the absorption column 210. Continuously cycling flow of BTX-rich solvent from the absorption column 210, through the flash drum 235, to the distillation tower 250, and BTX-lean solvent back to the absorption column 210 provides an improved process for extracting BTX from a BTX-rich hydrocarbon gas feed stream.

TABLE 1

| Compound | Gas BTX Content (lb/hr) | Extracted BTX (lb/hr) | BTX Extraction Efficiency (%) |
|---|---|---|---|
| Benzene | 4761 | 4717 | 99.1 |
| Toluene | 4692 | 4689 | 99.9 |
| Xylene | 1778 | 1777 | 100.0 |
| Total | 11231 | 11183 | 99.6 |

Table 1 shows non-limiting example values of a simulation for a gas stream that is contacted with a liquid stream of sulfolane, and the extraction efficiency (individually and collectively) of BTX. As shown in Table 1, 99.1% of the benzene in the gas stream is removed from the gas stream, 99.9% of the toluene is removed from the gas stream, and 100% of the xylene is removed from the gas stream.

TABLE 2

| Flow Rate | Feedstock Composition | (mol %) | (lb/hr) | BTX-Free Gas (mol %) | Result (lb/hr) | BTX Product % | BTX Recovery |
|---|---|---|---|---|---|---|---|
| 650 MMSCFD | Methane | 87.17 | | 87.4 | | | |
| | Ethane | 1.50 | | 1.5 | | | |
| | Propane | 0.24 | | 0.2 | | | |
| | i-Butane | 0.04 | | 0.0 | | | |
| | n-Butane | 0.08 | | 0.0 | | | |
| | i-Pentane | 0.03 | | 0.0 | | | |
| | n-Pentane | 0.02 | | 0.0 | | | |
| | Hexane | 0.03 | | 0.0 | | | |
| | Nitrogen | 7.85 | | 7.9 | | | |
| | $CO_2$ | 2.90 | | 2.9 | | | |
| | $H_2S$ | 0.00 | | 0.0 | | | |
| | $H_2O$ | Satur. | | Satur. | | | |
| | Benzene (ppm) | 490 | 2734 | 2.6 | 14.5 | 2692 | 97.5 |
| | Toluene (ppm) | 392 | 2580 | 0.0 | 0.92 | 2379 | 99.0 |
| | Xylene (ppm) | 196 | 1486 | 0.0 | 0.22 | 1486 | 99.0 |

Table 2 shows non-limiting example values of another simulation for a gas stream that is contacted with a liquid stream of sulfolane, and the extraction efficiency (individually and collectively) of BTX. As shown in Table 2, 97.5% of the benzene in the gas stream is removed from the gas stream, 99.0% of the toluene is removed from the gas stream, and 99.0% of the xylene is removed from the gas stream.

Figure 3:
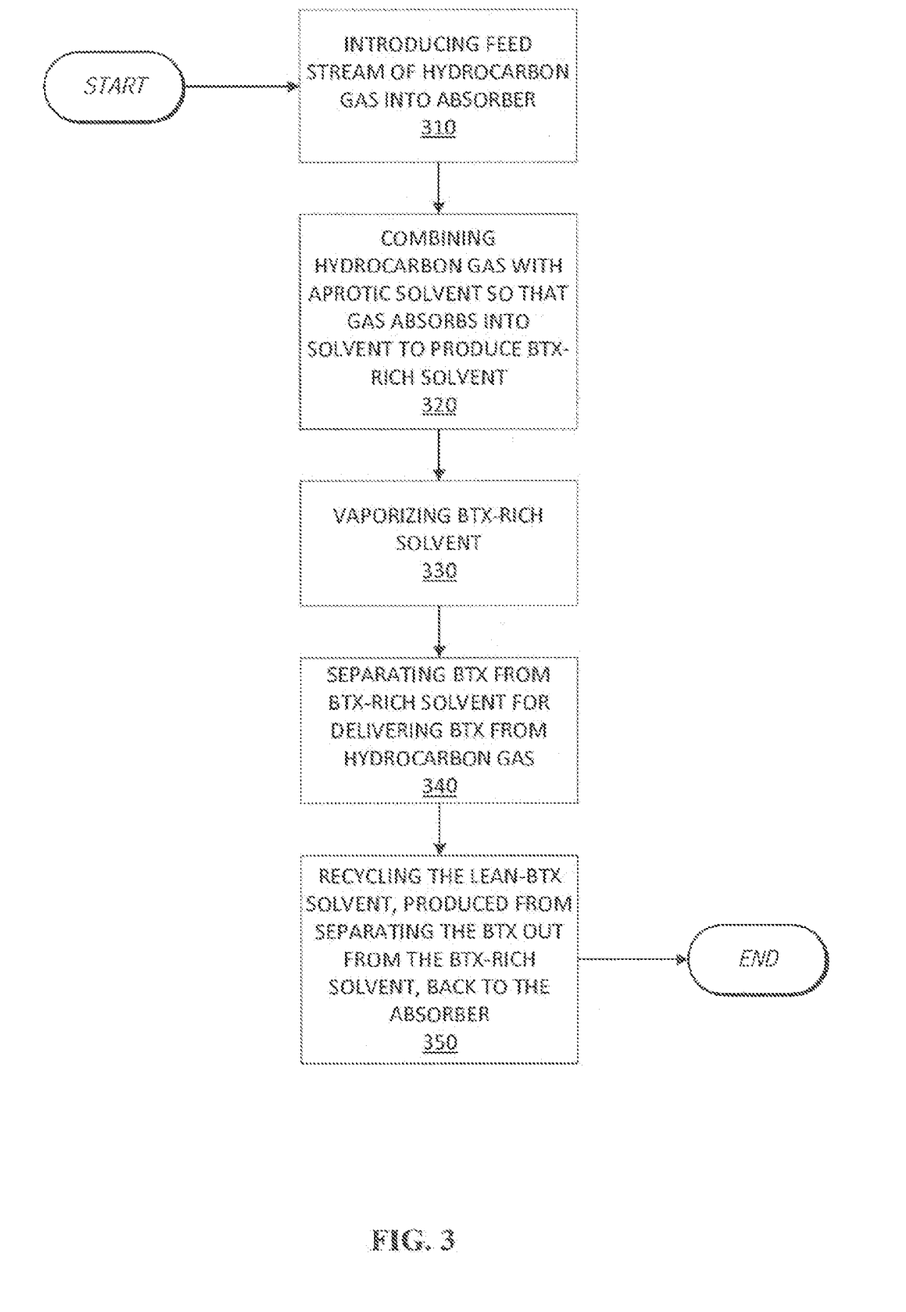
FIG. 3 is a flow diagram of a recovery method for delivering extracted BTX from a hydrocarbon gas stream, in accordance with an embodiment of the invention.

FIG. 3 is a flow diagram of a recovery method for delivering extracted BTX from a hydrocarbon gas stream, in accordance with an embodiment of the invention. In accordance with an embodiment of the invention, the recovery method includes introducing, at step 310, a feed stream of a BTX-rich hydrocarbon gas into the absorption column 210, as shown in FIG. 2. The hydrocarbon gas is combined, at step 320, with an aprotic solvent in the absorption column 210, such that the hydrocarbon gas and the aprotic solvent are thoroughly intermixed so that the BTX in the BTX-rich hydrocarbon gas is absorbed into the aprotic solvent to produce a BTX-rich solvent and a substantially BTX-free gas. The BTX-rich solvent is vaporized, at step 330, in the flash drum 235, as shown in FIG. 2, to produce a vaporized BTX-rich solvent. In accordance with at least one embodiment, the flash drum 235 is operated at about 100° F. and about 100 psig.

The recovery method further includes feeding, at step 340, the vaporized BTX-rich solvent to the distillation tower 250, as further shown in FIG. 2, where the BTX is separated from the vaporized BTX-rich solvent for delivering the extracted BTX from the hydrocarbon gas. In accordance with an embodiment of the invention, the method further includes separating, at step 350, the BTX from the vaporized BTX-rich solvent to produce a BTX-lean solvent. The BTX-lean solvent is recycled back into the absorption column 210 as the aprotic solvent. As discussed above, the aprotic solvent includes, for example, an organosulfur solvent such as tetramethylene sulfone.

In accordance with one embodiment of the invention, the hydrocarbon gas is combined with the aprotic solvent in a ratio of 15 US gallons of aprotic solvent to 1 pound of benzene in the feed stream of the hydrocarbon gas.

In accordance with another embodiment of the invention, the feed stream of the hydrocarbon gas is fed into the absorption column 210, as shown in FIG. 2, below a feed stream for the aprotic solvent (i.e., for the BTX-lean solvent recycled from the distillation tower 250), so that the hydrocarbon gas flows upward within the absorption column 210 to contact the aprotic solvent to be absorbed into the aprotic solvent.

In accordance with another embodiment of the invention, the absorption column 210 is pressurized to a predefined pressure, before feeding the BTX-lean solvent into the absorption column 210, to overcome a pressure loss in a feed stream of the BTX-lean solvent into the absorption column 210. For example, according to one embodiment of the invention, the absorption column 210 is pressurized to about 800 to about 900 psig. In accordance with at least one embodiment, the absorption column 210 is operated at about 100° F.

Figure 4:
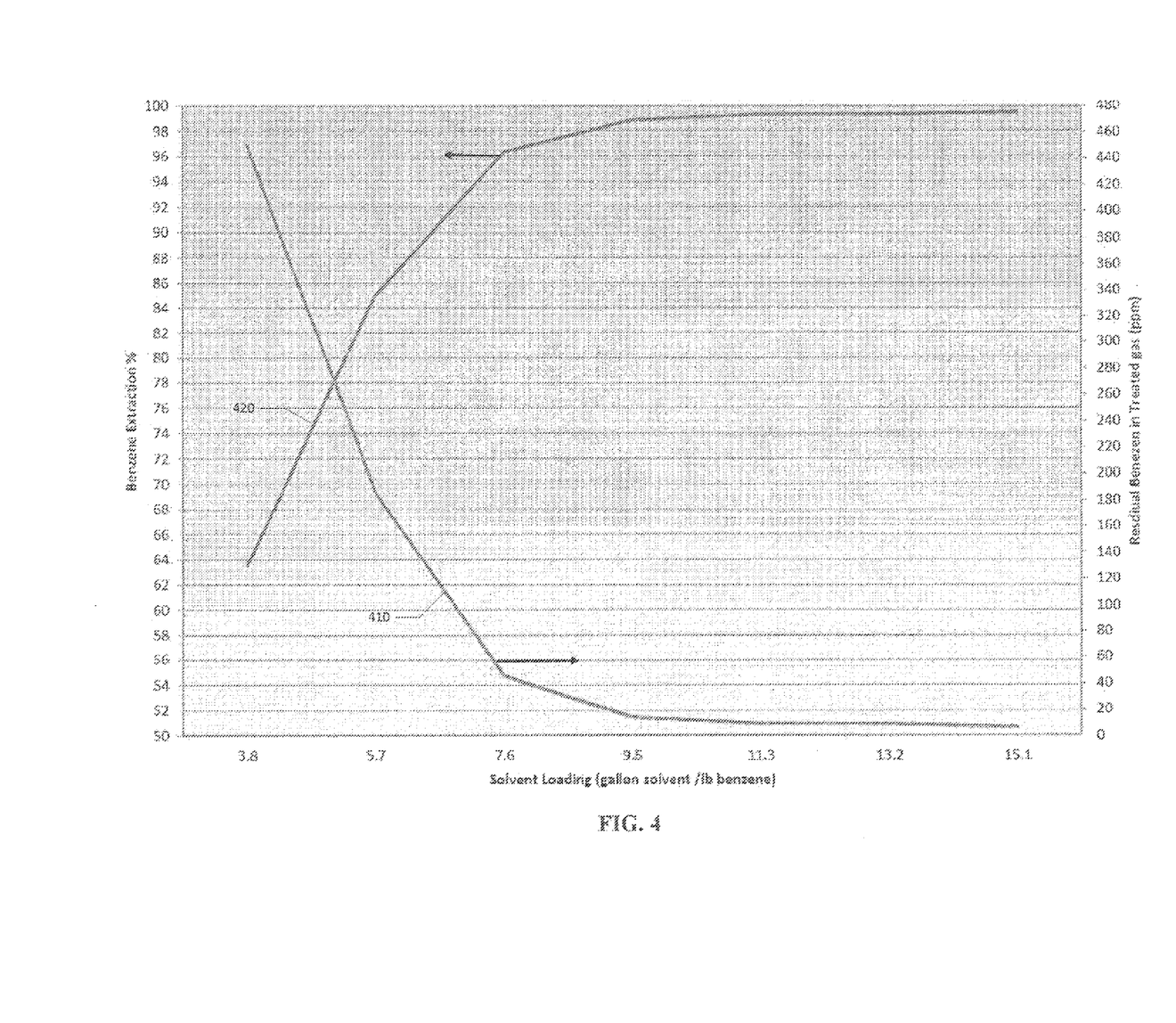
FIG. 4 is a graph representing solvent loading versus percentage of benzene extracted and residual benzene resulting from the recovery system, as shown in FIG. 2, and the recovery method, as shown in FIG. 3, in accordance with various embodiments of the invention.

FIG. 4 is a graph representing solvent loading versus percentage of benzene extracted and residual benzene resulting from the recovery system as shown in FIG. 2 and the recovery method as shown in FIG. 3, in accordance with various embodiments of the invention. FIG. 4 shows how varying solvent loading affects the amount of residual benzene remaining in the product gas in the treated gas line 225 extending from the upper end of the absorption column 210 (see line 410). FIG. 4 also shows how varying solvent loading affects the percentage of benzene extracted from the BTX-rich hydrocarbon feed stream in the feed stream line 205 (see line 420).

In accordance with various embodiments of the invention, solvent loading describes a ratio of gallons of sulfolane flowing in the reflux line 220 versus pounds of benzene in the BTX-rich hydrocarbon gas in the feed stream line 205. As shown in the example of FIG. 4, when a solvent loading ratio is at around 3.8, residual benzene in the treated gas is about 450 ppm and the percentage of benzene that is extracted is about 63.5%; when the solvent loading ratio is at around 5.7, residual benzene in the treated gas is about 190 ppm and the percentage of benzene that is extracted is about 85%; when the solvent loading ratio is at around 7.6, residual benzene in the treated gas is about 60 ppm and the percentage of benzene that is extracted is about 96%; when the solvent loading ratio is at around 9.5, residual benzene in the treated gas is about 15 ppm and the percentage of benzene that extracted is about 98.5%; when the solvent loading ratio is at around 11.3, residual benzene in the treated gas is about 10 ppm and the percentage of benzene that is extracted is about 99%; when the solvent loading ratio is at around 13.2, residual benzene in the treated gas is about 8 ppm and the percentage of benzene that is extracted is about 99.2%; and when the solvent loading ratio is at around 15:1, residual benzene in the treated gas is about 5 ppm and the percentage of benzene that is extracted is about 99.5%.

Embodiments of the invention provide non-obvious advantages over conventional adsorption systems used for gas streams and absorption systems used for liquid streams. For example, certain embodiments provide recovery methods and systems for delivering an extracted BTX component from a BTX-rich hydrocarbon gas stream that includes contacting, in an amine-free environment, a BTX-rich hydrocarbon gas feed stream with an aprotic solvent to produce a substantially BTX-free gas and a BTX component. Because it is not consumed, the BTX component can be recovered, for example, for use as a petrochemical feedstock or for other commercial uses. Embodiments of the invention can be used to remove unwanted chemicals from a sales gas stream by extracting the BTX from the sales gas stream and recovering the BTX in a distillation portion of the process. As a result, the constituents of the recovered BTX may be marketed and sold for other commercial uses.

The present invention may suitably comprise, consist or consist essentially of the elements disclosed and may be practiced in the absence of an element not disclosed. For example, it can be recognized by those skilled in the art that certain steps can be combined into a single step.

Unless defined otherwise, all technical and scientific terms used have the same meaning as commonly understood by one of ordinary skill in the art to which this invention belongs.

The singular forms "a," "an," and "the" include plural referents, unless the context clearly dictates otherwise.

As used herein and in the appended claims, the words "comprise," "has," and "include" and all grammatical variations thereof are each intended to have an open, non-limiting meaning that does not exclude additional elements or steps.

"Optionally" means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

What is claimed is:

1. A recovery method for delivering extracted benzene, toluene and xylene from a gas stream in an amine-free environment, the method comprising:

introducing a feed stream of a hydrocarbon gas into an absorber, the hydrocarbon gas comprising the benzene, toluene and xylene;

combining, in the absorber, the hydrocarbon gas with an aprotic solvent, such that the hydrocarbon gas and the aprotic solvent are thoroughly intermixed so that the benzene, toluene and xylene are absorbed into the aprotic solvent, resulting in a benzene, toluene and xylene-rich solvent;

vaporizing, using a vaporizer, the benzene, toluene and xylene-rich solvent, resulting in a vaporized benzene, toluene and xylene-rich solvent; and separating, using a distiller; the benzene, toluene and xylene from the vaporized benzene, toluene and xylene-rich solvent for delivering the extracted benzene, toluene and xylene from the hydrocarbon gas at an extraction efficiency percentage of greater than about 99%, wherein the percentage of benzene, toluene and xylene that is recovered is greater than about 95%.

2. A recovery method as defined in claim 1, wherein the separating the benzene, toluene and xylene from the vaporized benzene, toluene and xylene-rich solvent produces a benzene, toluene and xylene-lean solvent, the benzene, toluene and xylene-lean solvent being fed into the absorber as the aprotic solvent.

3. A recovery method as defined in claim 1, wherein the combining comprises intermixing the hydrocarbon gas with the aprotic solvent in a ratio of 15 US gallons of aprotic solvent to 1 pound of benzene in the feed stream of the hydrocarbon gas.

4. A recovery method as defined in claim 1, wherein the combining comprises intermixing the hydrocarbon gas with the aprotic solvent, the aprotic solvent being an organosulfur solvent.

5. A recovery method as defined in claim 1, wherein the introducing the feed stream of the hydrocarbon gas comprises feeding the hydrocarbon gas into the absorber below a feed stream for the aprotic solvent, so that the hydrocarbon gas flows upward within the absorber to contact the aprotic solvent to be absorbed into the aprotic solvent.

6. A recovery method as defined in claim 1, wherein the combining comprises intermixing the hydrocarbon gas with the aprotic solvent, so that the benzene, toluene and xylene are absorbed into the aprotic solvent, resulting in a production of a BTX-free gas.

7. A recovery method as defined in claim 6, wherein the BTX-free gas comprises less than about 4% of the benzene, toluene and xylene originally contained in the feed stream of the hydrocarbon gas introduced into the absorber.

8. A recovery method as defined in claim 2, further comprising:

pressurizing the absorber to a predefined pressure, before feeding the benzene, toluene and xylene-lean solvent into the absorber, to overcome a pressure loss in a feed stream of the benzene, toluene and xylene-lean solvent into the absorber.

9. A recovery method as defined in claim 8, wherein the absorber is pressurized between about 800 to about 900 psig.

* * * * *

UNITED STATES PATENT AND TRADEMARK OFFICE
CERTIFICATE OF CORRECTION

PATENT NO. : 9,090,521 B2  
APPLICATION NO. : 13/828700  
DATED : July 28, 2015  
INVENTOR(S) : Mohammad N. Al-Haji Page 1 of 1

It is certified that error appears in the above-identified patent and that said Letters Patent is hereby corrected as shown below:

In the Claims

In Column 9, Line 1, Claim 1, the word appears as "distiller;" and should read --distiller,--.

Signed and Sealed this
Nineteenth Day of April, 2016

Michelle K. Lee
*Director of the United States Patent and Trademark Office*